United States Patent

Shu et al.

[11] Patent Number: 5,833,925
[45] Date of Patent: Nov. 10, 1998

[54] AUTOMATIC CHEMISTRY ANALYZER WITH IMPROVED ION SELECTIVE ELECTRODE ASSEMBLY

[75] Inventors: Frank R. Shu, La Habra; Daniel J. Wilson, Quail Valley; Bradley A. Butcher, La Verne, all of Calif.

[73] Assignee: Beckman Instruments, Inc., Fullerton, Calif.

[21] Appl. No.: 746,560

[22] Filed: Nov. 13, 1996

[51] Int. Cl.$^6$ .................................................. G01N 35/10
[52] U.S. Cl. .......................... 422/63; 422/81; 422/82.03; 422/100; 422/103; 436/43; 436/47; 436/54; 436/180; 251/129.17; 417/415; 417/534; 417/536
[58] Field of Search .................... 422/63, 64, 68.1, 422/73, 81, 100, 103; 436/43, 47, 49, 54, 174, 179, 180; 251/129.17; 417/410.1, 415, 521, 534, 536

[56] References Cited

U.S. PATENT DOCUMENTS

| | | |
|---|---|---|
| 159,533 | 2/1875 | Westinghouse, Jr. .................... 417/534 |
| 4,200,607 | 4/1980 | Suzuki ...................................... 422/64 |
| 4,512,953 | 4/1985 | Marsoner et al. ........................ 422/67 |
| 4,627,795 | 12/1986 | Schmitz-Montz ....................... 417/267 |
| 4,873,057 | 10/1989 | Robertson et al. ...................... 422/75 |
| 4,888,998 | 12/1989 | Buzza et al. . |
| 4,920,056 | 4/1990 | Dasgupta .................................. 436/50 |
| 4,944,487 | 7/1990 | Holtermann ............................ 251/129 |
| 4,965,049 | 10/1990 | Lillig et al. . |
| 5,213,762 | 5/1993 | Ricchio et al. . |
| 5,223,222 | 6/1993 | Ricchio et al. . |
| 5,265,843 | 11/1993 | Kleinhappl ......................... 251/129.17 |
| 5,395,588 | 3/1995 | North, Jr. et al. ....................... 422/84 |
| 5,505,593 | 4/1996 | Hartley et al. .......................... 417/393 |
| 5,542,452 | 8/1996 | Carver, Jr. et al. ............... 137/625.48 |
| 5,653,422 | 8/1997 | Pieloth et al. ....................... 251/129.2 |
| 5,679,575 | 10/1997 | Kubota et al. ............................ 436/49 |

Primary Examiner—Long V. Le
Attorney, Agent, or Firm—William H. May; P. R. Harder; Sheldon & Mak

[57] ABSTRACT

An ion selective electrode assembly is provided having a sample injection cup, a flow cell analyzer and multiple module pump for simultaneously pumping liquids between the sample injection cup and the flow cell analyzer using a single motor. One of the pump modules is capable of pumping a reference solution directly to the flow cell analyzer. Flow through each pumping module is controlled by a pair of rocker valves. The sample injection cup includes a first diaphragm valve for allowing a mixture of sample and reagent to flow to the flow cell analyzer. The sample injection cup further includes a second diaphragm valve installed immediately downstream of the first diaphragm for allowing a flushing solution to flow throughout the sample injection cup and the flow cell analyzer.

7 Claims, 13 Drawing Sheets

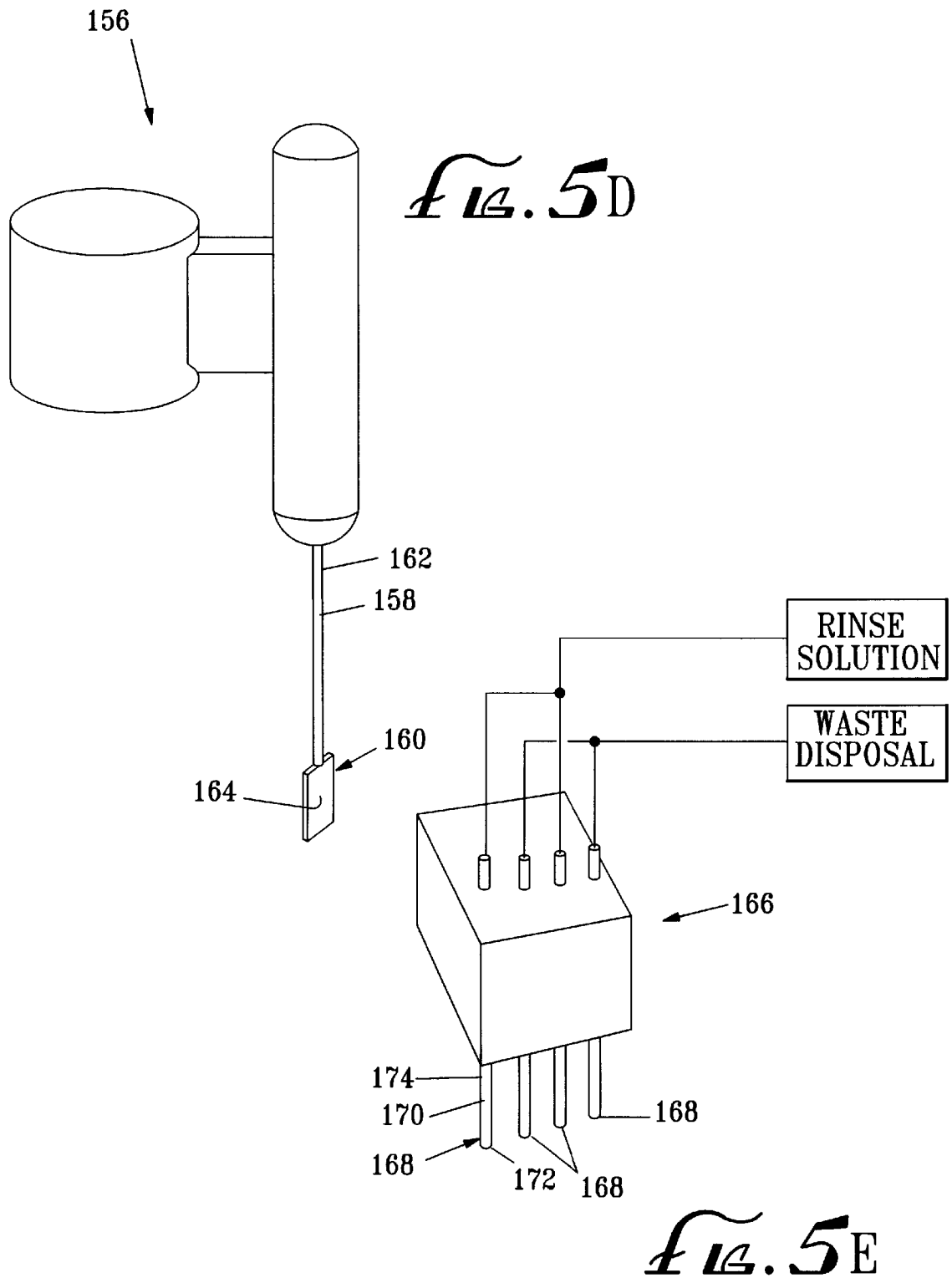

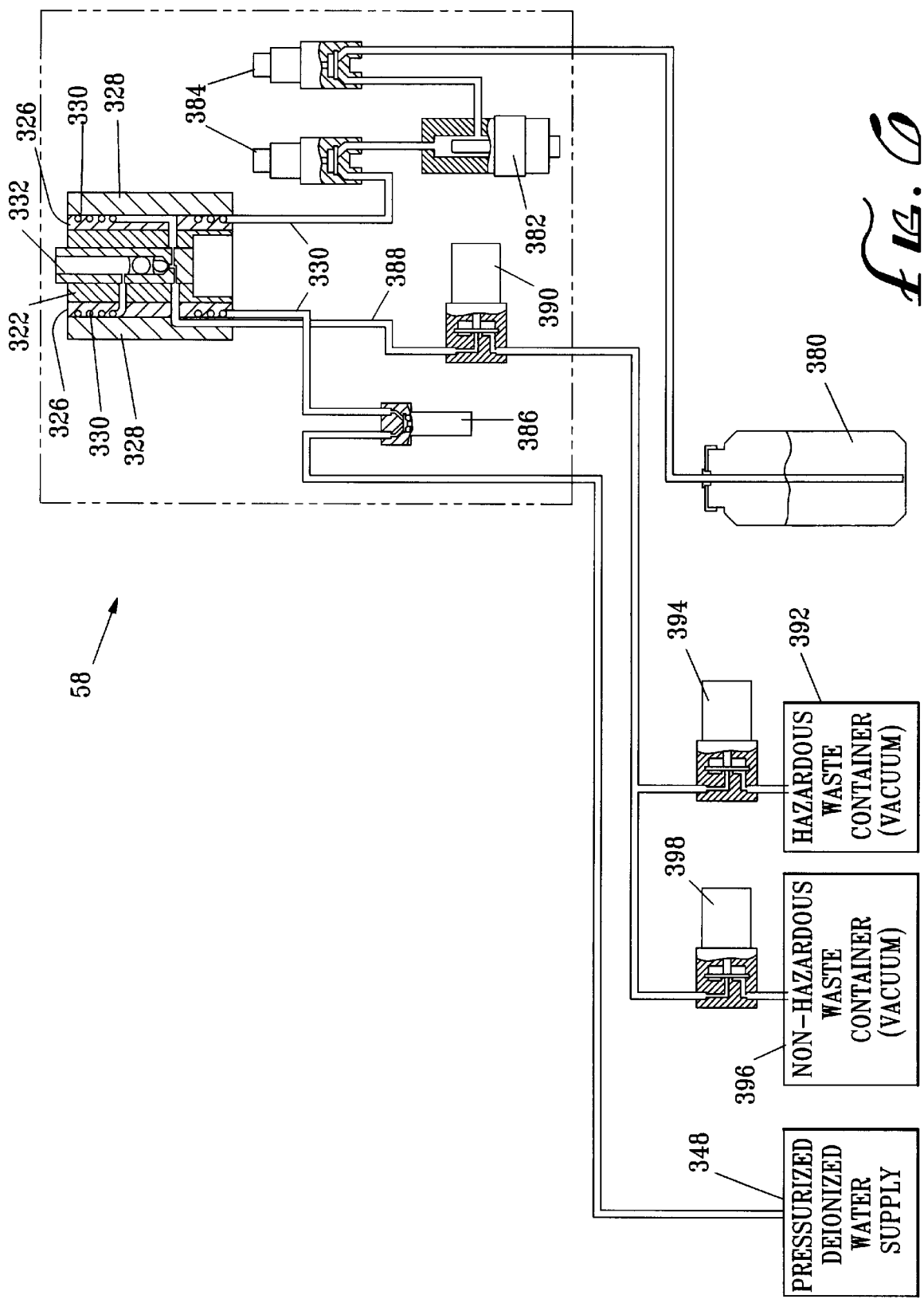

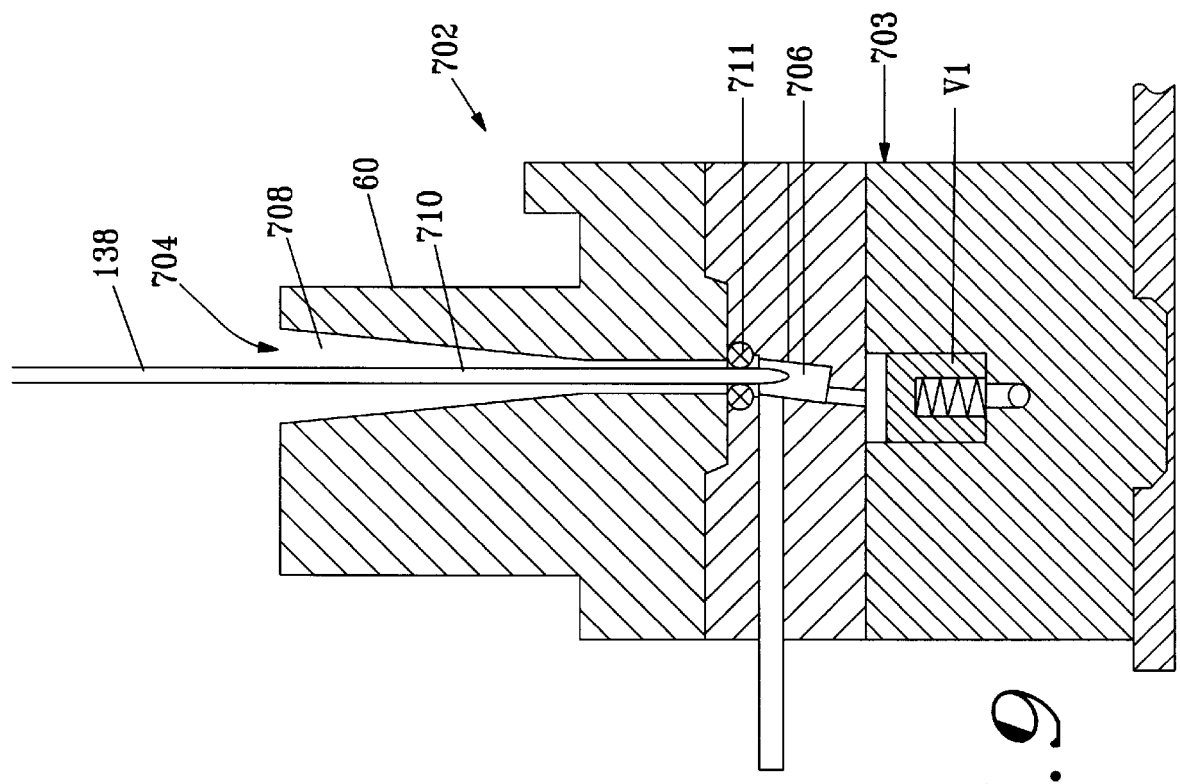
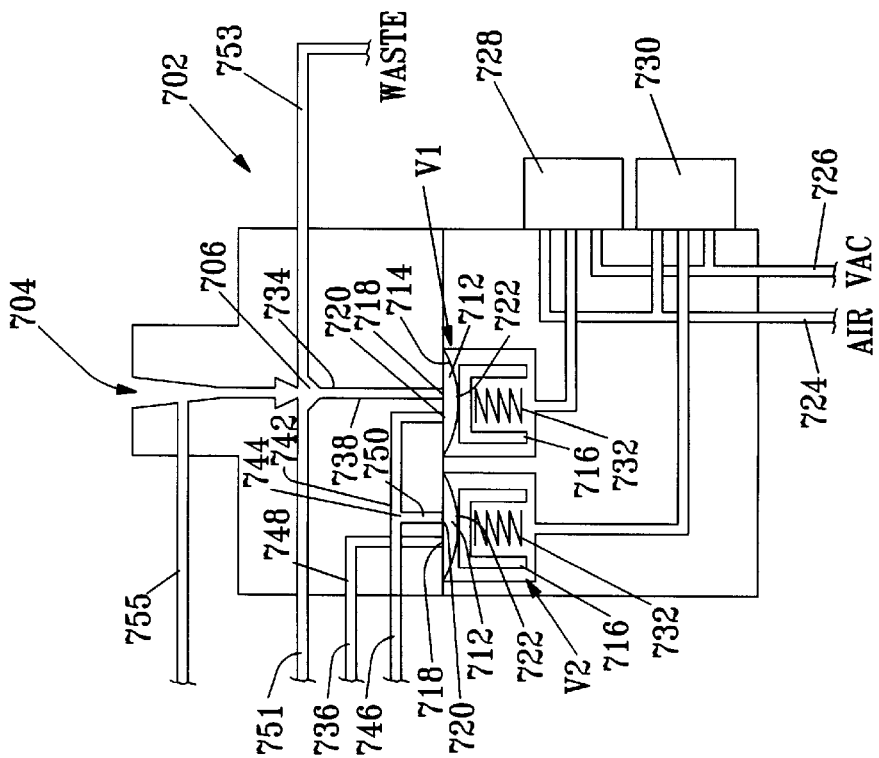
fig. 9
fig. 10

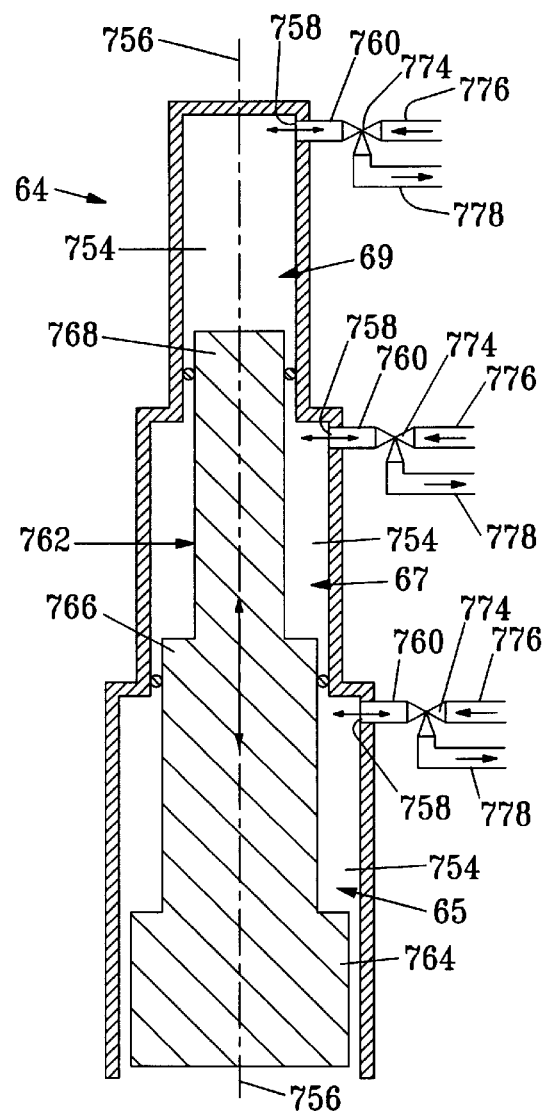
*fig.11*
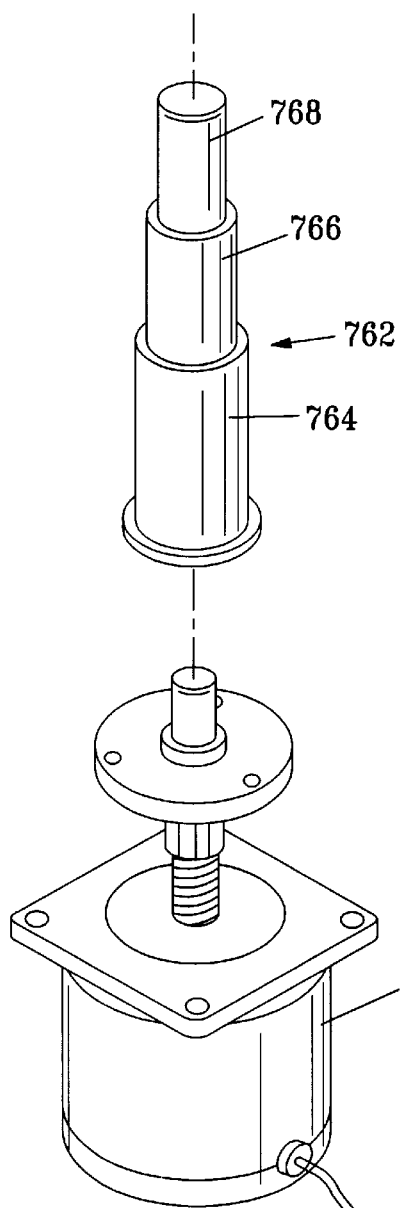
*fig.12*
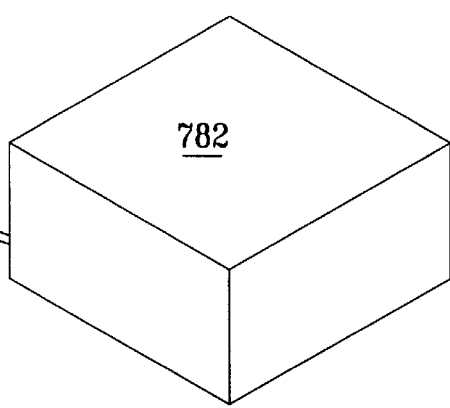

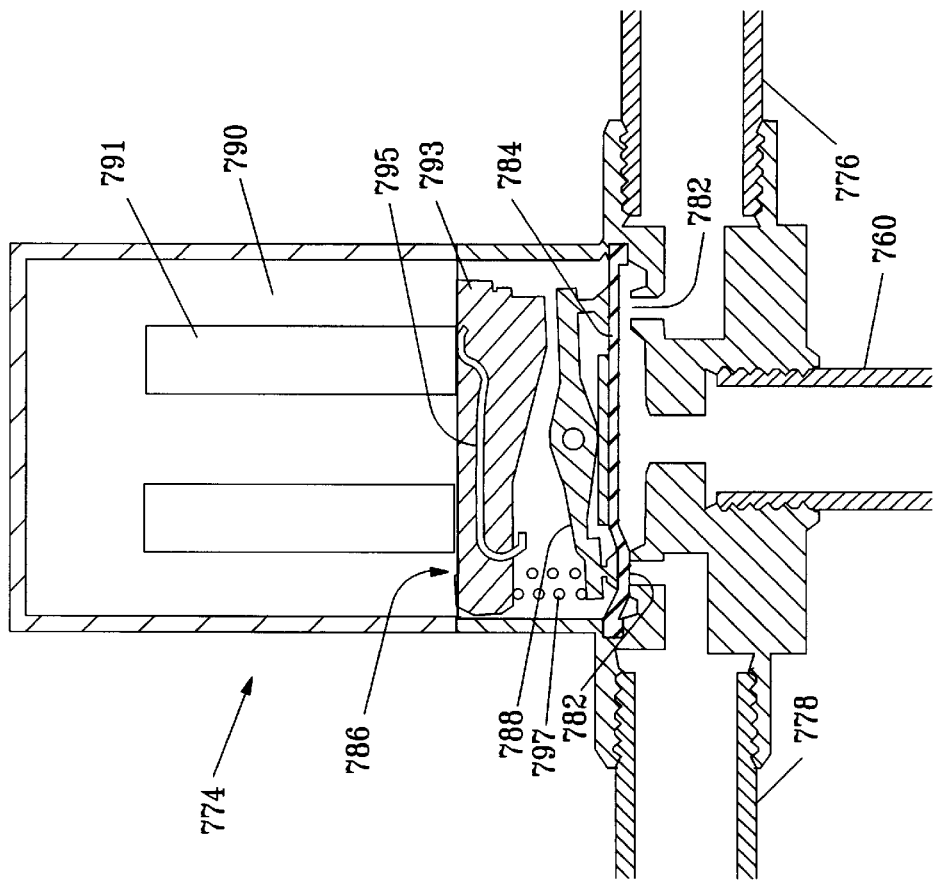
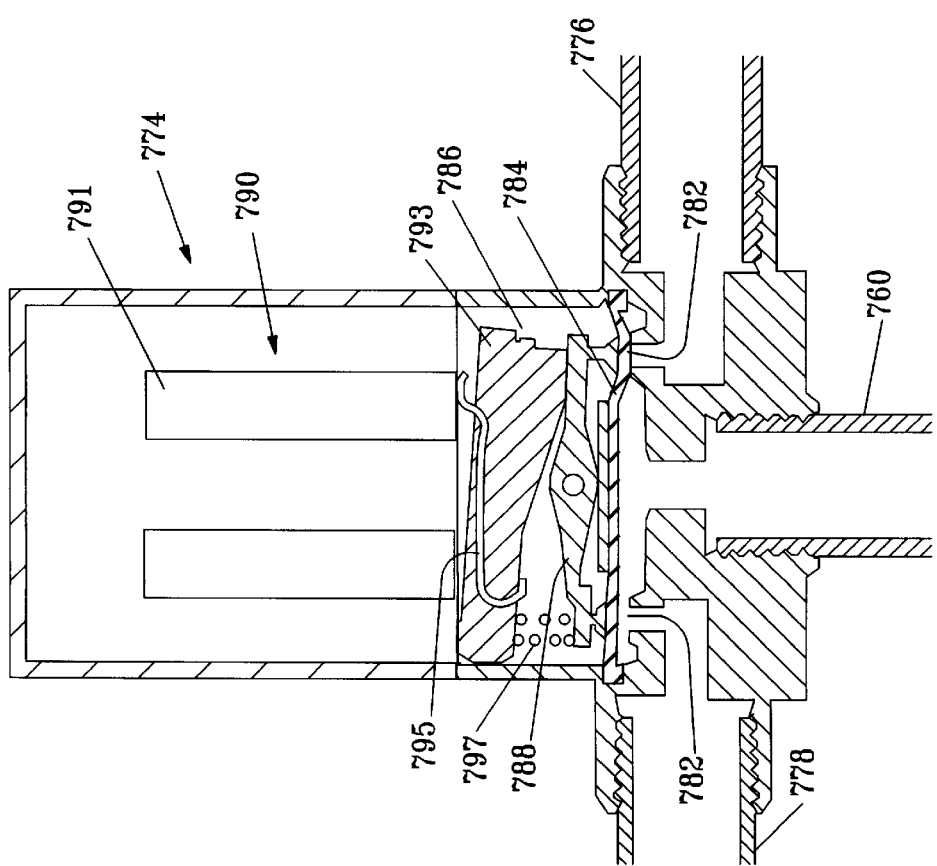

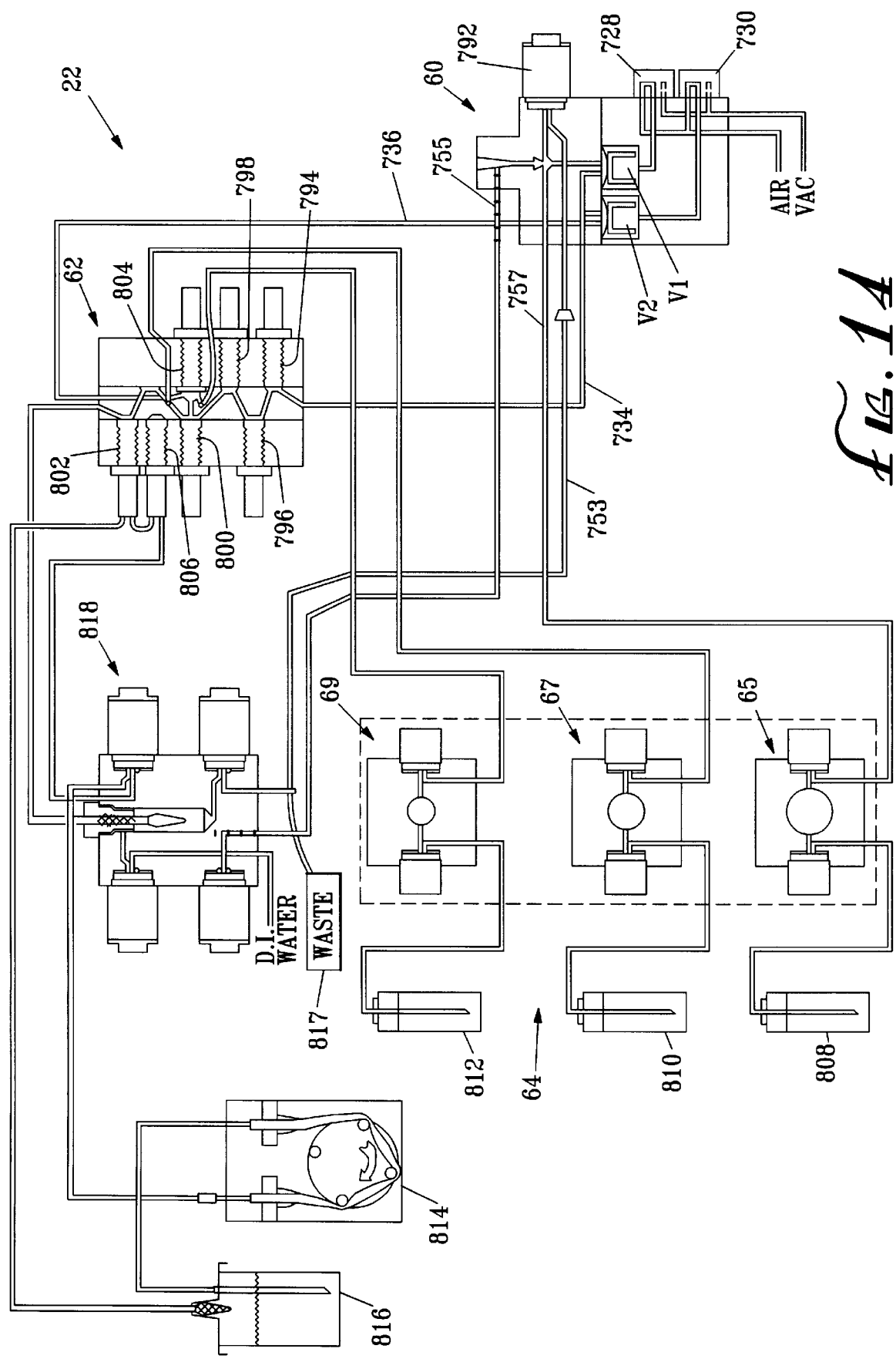

AUTOMATIC CHEMISTRY ANALYZER WITH IMPROVED ION SELECTIVE ELECTRODE ASSEMBLY

FIELD OF THE INVENTION

This invention generally relates to the field of automated clinical chemical analyzers, and specifically to high throughput automated chemical analyzers having ion selective electrode analyzer modules.

BACKGROUND OF THE INVENTION

A number of different automated clinical chemical analyzers are known in the art. Such analyzers range from simple, largely manually operated instruments to highly complex, nearly fully automated instruments. Each analyzer has its own particular performance characteristics related to the number ("menu") of different tests that the analyzer can perform and the number of samples that can be processed in a given period of time ("throughput").

Large scale, highly complex analyzers useful in large hospitals and clinical laboratories have been developed which have both a large menu of tests which the instrument can perform and a high throughput. Such an analyzer is described in U.S. Pat. No. 4,965,049 issued to Lillig et al. which is incorporated herein by reference in its entirety.

Such large scale, highly complex analyzers typically employ an ion selective analyzing station having an upstream sample injection cup and a downstream flow cell analyzer. Such an ion selective analyzing station can simultaneously analyze a liquid sample for a wide variety of electrolytes. In a typical ion selective analyzing station, a predetermined quantity of sample is flow-mixed with a predetermined quantity of a reagent in a sample reaction cup. The resulting mixture of sample and reagent is then pumped through a flow cell analyzer wherein specialized electrode cells emit signals proportional to the relative quantities of the various electrolytes in the sample.

As sophisticated as such prior art ion selective analyzing stations have become, problems remain. One problem is how to efficiently flush the sample reaction cup between cycles. Sample reaction cups of the prior art typically have relatively long conduit sections which cannot be easily flushed between analysis cycles.

Another problem in the prior art is the common use of a reagent pump comprising a stepper motor which drives rotary cam pinch valve mechanisms. Such pinch valve mechanisms pinch and unpinch tubing sections within the pump stages to create a pumping action. However, in such pumps, the cam shape (permanently built into the pump) controls when each pump is pinched closed. Accordingly, valve timing is machined into the cam and is not adjustable. Moreover, such pumps require frequent operator attention to "massage" the tubing so that it will open and close correctly. Moreover, such pumps require accurate and frequent adjustments of certain gap settings. Such adjustments generally must be accomplished by trained technical personnel. In general, such pumps require an excessive amount of maintenance.

Another problem with ion selective analyzing stations of the prior art is that they typically require that internal referencing solutions—solutions necessary in calibrating the station between each analyzing cycle—be brought into the flow cell analyzer by the same aspiration/ejection probe which is used to transport sample to the sample reaction cup. This additional required use of the aspiration/ejection probe necessarily requires additional aspiration/ejection probe time, and thereby increases the time required for each analysis cycle.

Accordingly, there is a need for an ion selective analyzing station wherein the sample reaction cup can be efficiently and nearly completely cleaned between each analysis cycle.

There is further a need for an ion selective analyzing station which does not rely on a pump requiring pinch valves.

Still further, there is a need for an ion selective analyzing station wherein internal reference solution can be dispensed to the flow cell analyzer without the use of the aspiration/ejection probe.

SUMMARY OF THE INVENTION

The invention satisfies these needs. The invention is an ion selective electrode analyzing combination comprising (a) a sample injection cup having a sample cup mixing chamber and a sample cup outlet opening, (b) a flow cell for measurement of different electrolytes in a liquid sample, the flow cell having a flow cell inlet opening and a flow cell outlet opening, (c) a pump having a plurality of discrete pumping modules and a first pump motor for driving all of the pumping modules, each pumping module having a pumping module inlet opening and a pumping module outlet opening, (d) a first conduit for connecting the sample injection cup outlet opening in fluid tight communication to the flow cell inlet opening, the first conduit having therein a first valve disposed proximate to the sample cup outlet opening, and (e) a second conduit for connecting the outlet opening of one of the pumping modules to the first conduit at a location immediately downstream of the first valve, the second conduit having therein a second valve.

In a typical embodiment, the combination is capable of determining some or all of the following electrolytes: sodium, potassium, calcium, chloride and carbon dioxide.

In a preferred embodiment, the first and second valves comprise (a) a valve chamber having a valve inlet opening, a valve outlet opening and a valve seat, (b) a flexible membrane disposed within the valve chamber proximate to the valve seat, and (c) an activator for alternatively (1) exerting pressure on the membrane so as to cause the membrane to flex to a first membrane position wherein the membrane is tightly disposed against the valve seat and no liquid is allowed to flow through the first valve and (2) withdrawing pressure from the membrane so as to cause the membrane to flex to a second membrane position wherein the membrane is not disposed against the valve seat and liquid is allowed to flow through the first valve, the activator being activatable by an energy source and the activator being constructed such that, in the event of a failure of the energy source, the activator flexes the membrane to the first membrane position.

In another preferred embodiment, the pump comprises (a) a first pumping chamber having a first inlet opening, a first outlet opening and a first central bore, the first central bore being aligned along a longitudinal axis, (b) a second pumping chamber having a second inlet opening, a second outlet opening and a second central bore, the second central bore being aligned along the longitudinal axis, (c) a reciprocatable piston disposed along the longitudinal axis, the piston having a first piston moiety disposed within the first bore and a second piston moiety disposed within the second bore, both first and second piston moieties being shaped with a large diameter section and a small diameter section, the piston being constructed to seal the first pumping chamber from the second pumping chamber, (d) a pump motor for reciprocating the first piston within the first bore and the second piston within the second bore, (e) a first inlet conduit attached in fluid tight communication with the first inlet opening, a first outlet conduit attached in fluid tight communication with the first outlet opening, a second inlet conduit attached in fluid tight communication with the second inlet opening and a second outlet conduit attached in fluid tight communication with the second outlet opening, and (f) a first inlet valve disposed within the first inlet conduit, a first outlet valve disposed within the first outlet conduit, a second inlet valve disposed within the second inlet conduit and a second outlet valve disposed within the second outlet valve.

Preferably, all of the valves comprise (a) a pair of valve seats, (b) a flexible diaphragm disposed opposite the valve seats, the diaphragm being capable of flexing between (1) a first diaphragm position wherein the diaphragm is sealed against the first first of the valve seats but not the second and (2) a second diaphragm position wherein the diaphragm is not sealed against the first of the valve seats but is sealed against the second, and (c) a flexing mechanism for alternatively flexing the diaphragm between the first diaphragm position and the second diaphragm position.

The invention is also an automated analyzing machine comprising the ion selective electrode analyzing combination described above.

The invention is also a method of using the ion selective electrode analyzing combination described above.

DESCRIPTION OF THE DRAWINGS

These and other features, aspects and advantages of the present invention will become better understood with reference to the following description, appended claims and accompanying drawings where:

FIG. 5D is a perspective view of a cuvette stirring rod assembly;

FIG. 5E is a perspective view of a cuvette wash station; and

FIG. 6 is a flow diagram illustrating a reaction cup combination useful in the invention;

FIG. 9 is a cross-sectional view of a sample reaction cup and valve combination having features of the invention;

FIG. 10 is a diagrammatic view of a sample reaction cup and valve combination having features of the invention;

FIG. 11 is a diagramatic view in partial cross-section of a pump having features of the invention;

FIG. 12 is a perspective view of a motor and reciprocating piston assembly useful in the pump illustrated in FIG. 11;

FIG. 13A is a cross-sectional view of a pump valve useful in the pump illustrated in FIG. 11, showing the valve a first valve position;

FIG. 13B is a cross-sectional view of the pump valve illustrated in FIG. 13A, but showing the valve in a second valve position; and FIG. 14 is a schematic view of an ion selective reaction cup assembly having features of the invention.

DETAILED DESCRIPTION

The following discussion describes in detail one embodiment of the invention and several variations of that embodiment. This discussion should not be construed, however, as limiting the invention to those particular embodiments. Practitioners skilled in the art will recognize numerous other embodiments as well. For a definition of the complete scope of the invention, the reader is directed to the appended claims.

Figure 1:
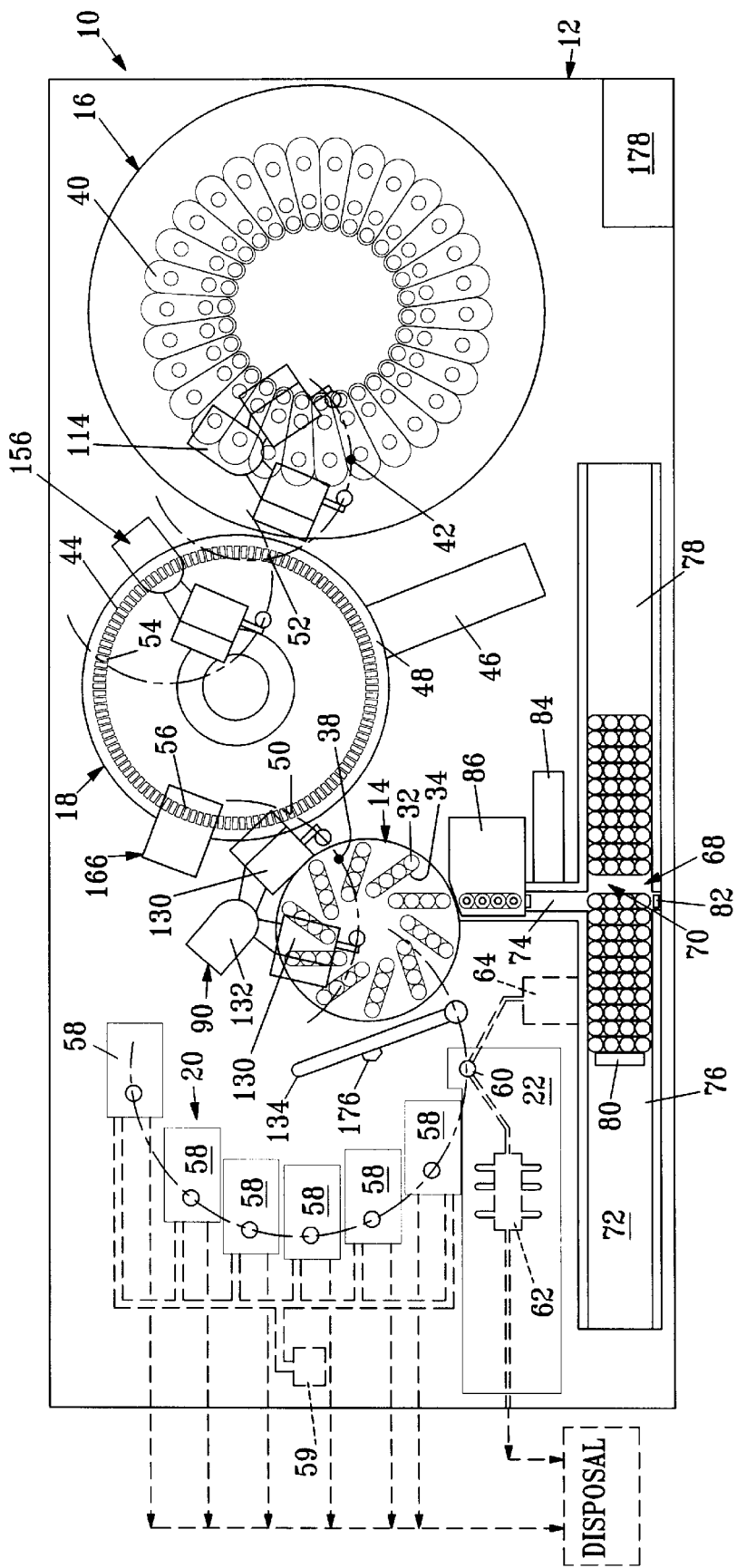
FIG. 1 is a schematic plan view of an automated analyzing machine having features of the invention.
Figure 2:
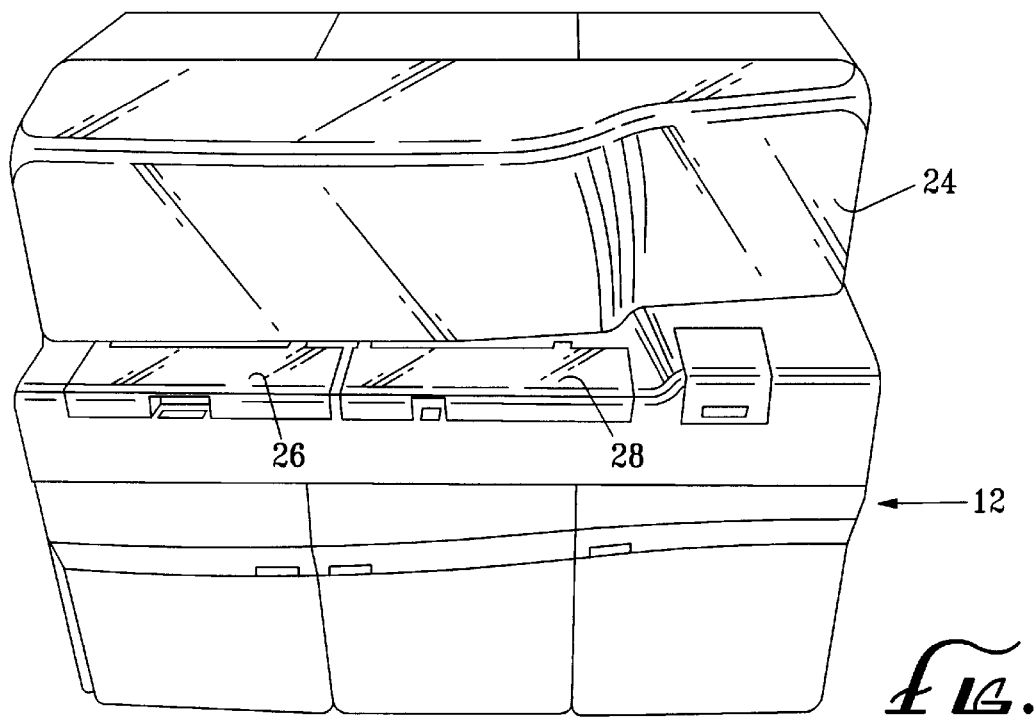
FIG. 2 is a front view of an automated analyzing machine having features of the invention with its canopy closed.
Figure 3:
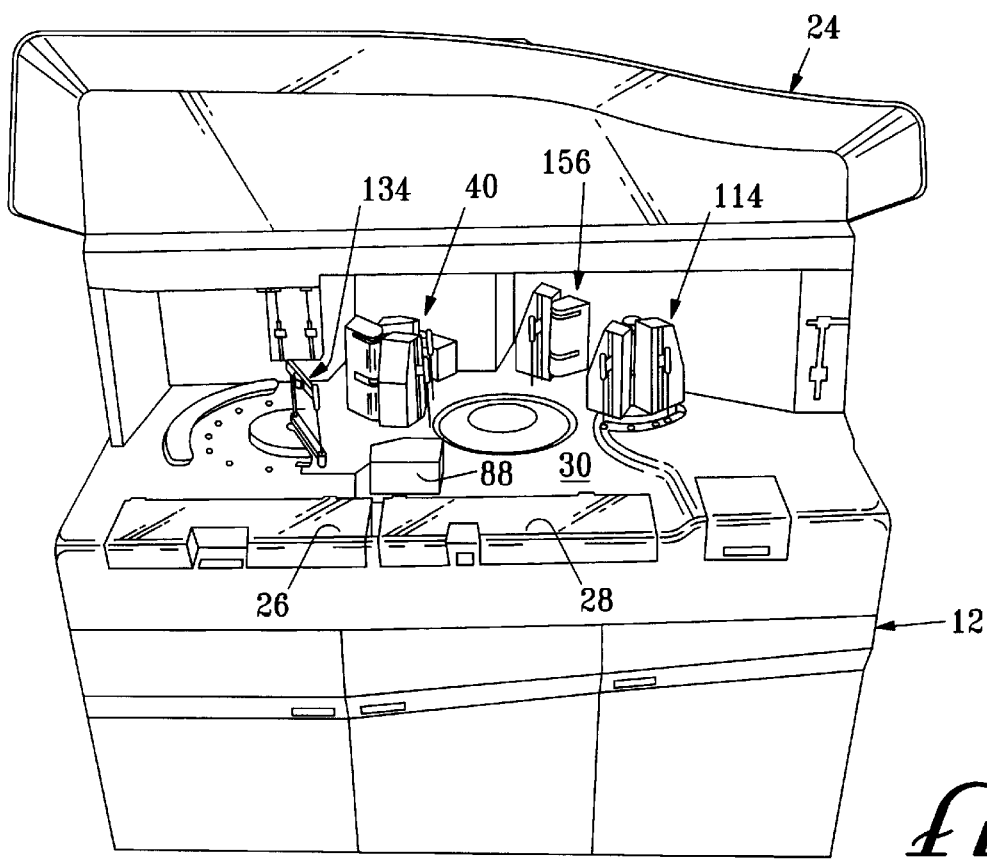
FIG. 3 is another front view of the automated analyzing machine of FIG. 2 shown with its canopy open.

FIGS. 1–3 show an automated analyzing machine 10 having features of the invention. The machine 10 comprises a body 12, a sample station 14, a reagent station 16, a random access analyzing station 18, a reaction cup analyzing station 20 and an ion selective electrode analyzing station 22.

The body 12 is typically a cabinet providing a housing for the various operative components. The body 12 is typically made from a lightweight metal such as a lightweight sheet steel. The embodiment shown in FIGS. 2 and 3 includes a hinged primary canopy 24. FIG. 2 shows the analyzing machine 10 with the primary canopy 24 closed. FIG. 2 shows the machine with the primary canopy 24 open.

FIGS. 2 and 3 also illustrate how a typical analyzing machine 10 of the invention can have an on-load tray cover 26, an off-load tray cover 28 and one or more operator area covers 30 covering the sample station 14, the reagent station 16, the random access analyzing station 18, the reaction cup analyzing station 20 and the ion selective electrode analyzing station 22.

Figure 4A:
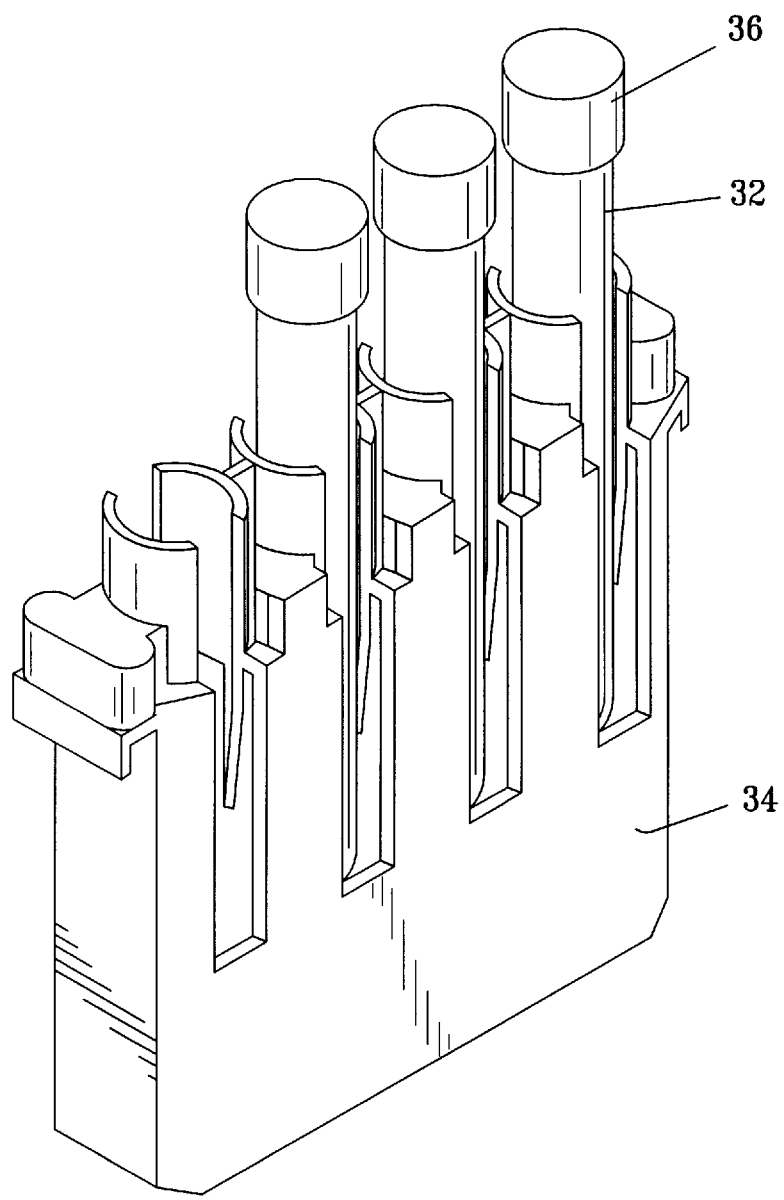
FIG. 4A is a perspective of a sample container rack useful in the invention.

The sample station 14 is sized and dimensioned to retain a plurality of sample containers 32. In the embodiment shown in FIGS. 1–3, the sample station 14 is a revolving circular carousel capable of retaining 40 sample containers 32 disposed in 10 sample container racks 34. In a typical embodiment, each sample container 32 is a generally upright container having a container cap 36 of thin rubber or like material. A sample container rack 34 containing four sample containers 32 useful in the invention is shown in FIG. 4A. The sample station 14 is moveable by a rotating motor (not shown) such that each sample container 32 can be alternatively positioned under and moved away from at least one sample extraction site 38.

The reagent station 16 is sized and dimensioned to retain a plurality of reagent containers 40. Each reagent container 40 contains one or more compartments for retaining one or more different reagents useful in the analysis chemistry performed by the analyzing machine 10. Also, it is preferable to predilute the reagent to minimize reagent usage and dilution step delays. A preferred reagent container 40 design has three individual compartments and is described in detail in U.S. Pat. Nos. 4,970,053 and 5,075,082, which are both incorporated herein by this reference in their entireties.

Preferably, the reagent station 16 is refrigerated, such as to a temperature of about 4° C., to preserve reagent life and minimize evaporation.

In the embodiment shown in FIGS. 1–3, the reagent station 16 is a revolving circular carousel. The reagent station 16 is movable by a rotating motor (not shown) such that each reagent container 40 can be alternatively positioned under and moved away from at least one reagent extraction site 42.

Preferably, the reagent station 16 also includes a bar code reader (not shown) which reads bar-coded information printed on the reagent containers 40 and/or disposed on the reagent carousel. Such information can be transmitted to a computerized controller to assist in operation of the analyzing machine 10.

Figure 4B:
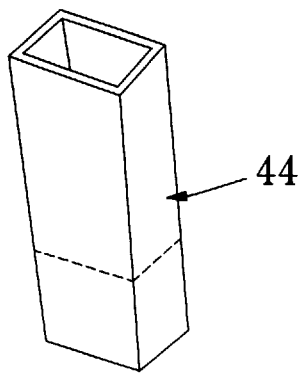
FIG. 4B is a perspective view of a reaction cuvette useful in the invention.
Figure 4C:
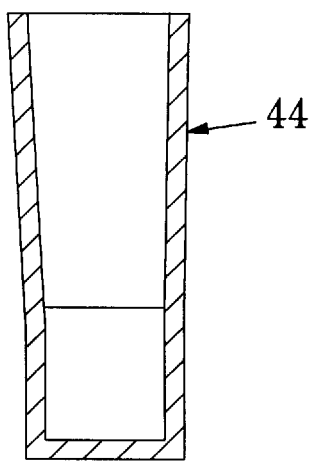
FIG. 4C is a cross-sectional side view of the reaction cuvette shown in FIG. 4B.

The random access analyzing station 18 is sized and dimensioned to retain a plurality of reaction cuvettes 44 as illustrated in FIGS. 4B and 4C. In the embodiment shown in FIGS. 1–3, the random access analyzing station 18 is a revolving circular carousel capable of retaining in excess of 100 cuvettes 44. Each cuvette 44 is a small open top reaction container having at least two opposed transparent sides through which a beam of light can be directed.

The random access analyzing station 18 further comprises random access analyzing station analyzer 46, such as a nephelometer and/or photometer disposed proximate to a random access analyzing station analyzing site 48 for determining at least one parameter of a sample disposed within the cuvettes 44.

The random access analyzing station 18 is movable by a rotating motor (not shown) such that each cuvette 44 can be alternatively positioned under and moved away from at least one cuvette sample deposit site 50, at least one cuvette reagent deposit site 52, at least one cuvette mixing site 54, at least one cuvette washing site 56 and the one random access analyzing station analyzing site 48.

The reaction cup analyzing station 20 comprises at least one reaction cup module 58. In the embodiment shown in FIG. 1, the reaction cup analyzing station 20 comprises six reaction cup modules 58. Each reaction cup module 58 can be used to measure high volume analyses such as analyses for sodium, potassium, glucose, creatinine and blood urea nitrogen.

FIG. 6 illustrates a flow scheme for a typical reaction cup module. Reagent is provided to a reaction cup 332 via an inlet conduit 330 on one side of the reaction cup module 58 (the right side on FIG. 6). Reagent is pumped from a source of reagent 380 by the reagent pump 59 through remote controllable reagent valves 384 into the inlet conduit 330. Within that portion of the inlet conduit 330 which is partially disposed within the reaction cup module 58, reagent is heated by a heating element 326 before flowing into the reaction cup 332. Deionized rinse water is provided to the reaction cup 332 from a pressurized source of deionized water 348 through a remote controllable deionized water valve 386 and into the inlet conduit 330 on the side of the reaction cup module 58 opposite the inlet conduit 330 through which reagent flows into the reaction cup 332. In that portion of the inlet conduit 330 which is disposed within the reaction cup module 58, deionized rinse water is heated by a second heating element 326 immediately prior to its flow into the reaction cup 332.

The reaction cup 332 is drained via a drain line 388 through a remote controllable master drain valve 390. When the liquid to be drained is of a potentially hazardous sort, the liquid is drained to a suitable hazardous waste container 392 through a remote controllable hazardous waste container valve 394. Where the liquid to be drained is of a non-hazardous sort, the liquid is drained to a suitable non-hazardous waste container 396 through a remote controllable non-hazardous waste container valve 398. Both the hazardous and non-hazardous waste containers 392 and 396 are typically maintained under vacuum to facilitate rapid and complete draining of liquid from the reaction cup 332. Because a separate deionized rinse water source 348 is provided to the reaction cup 332, such deionized rinse water is conveniently and inexpensively used in the rinsing step. Moreover, because water is used in the rinse steps, much of the liquid drained from the reaction cup during the rinsing step can be disposed in a non-hazardous waste disposal area. Note further that because two separate heating elements 326 are used, time lags required for heating are much reduced. This is especially true in analysis operations requiring multiple rinse cycles.

The use of the rinse water system also provides another substantial benefit over the prior art. The analyzing machine 10 using the cup analysis module 58 of the invention can be programmed to periodically and automatically recalibrate a nephelometer used as an analyzer 334, by briefly filling the reaction 332 cup with pure rinse water and calibrating the nephelometer to a predetermined set point. This eliminates having to periodically shut down the machine 10 and manually calibrating each of the nephelometers used in the various reaction cup modules 58.

A particularly useful reaction cup module 58 is disclosed in detail in U.S. patent application Ser. No. 08/746,560, entitled AUTOMATIC CHEMISTRY ANALYZER WITH IMPROVED ION SELECTIVE ELECTRODE ASSEMBLY (presently pending), filed contemporaneously herewith, and which is incorporated herein by reference in its entirety.

Figure 7:
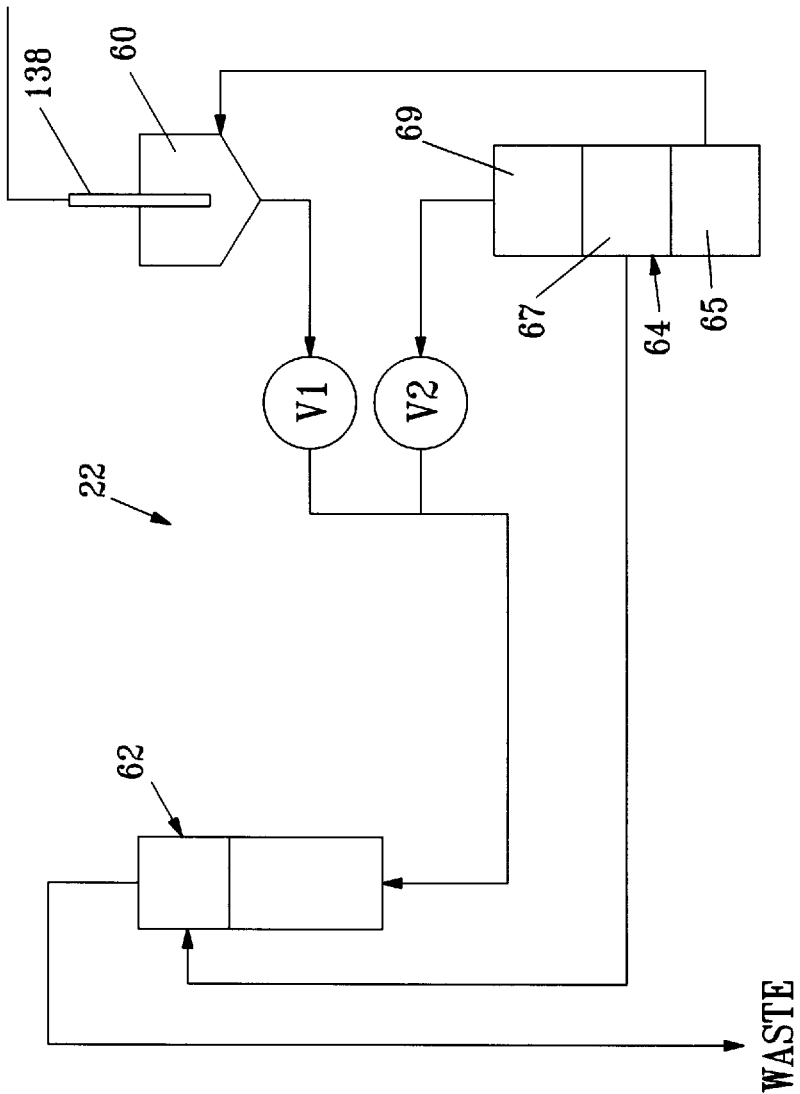
FIG. 7 is a flow diagram illustrating an ion selective reaction cup assembly having features of the invention.

FIG. 7 illustrates a simplified flow scheme for an ion selective analyzing station 22 of the invention. The ion selective electrode analyzing station 22 comprises a sample injection cup 60 disposed in fluid tight communication with a flow cell analyzer 62 is capable of measuring at least one electrolyte in a liquid sample. The ion selective electrode analyzing station 22 can be used to simultaneously analyze for sample electrolytes, such as sodium, potassium, calcium, chlorine and carbon dioxide. The sample injection cup 60 is disposed in fluid tight communication with an ion selective electrode analyzing station pump 64. The pump 64 comprises a reagent pump module 65 capable of pumping at least one ion selective electrode analyzing reagent from a source of such reagent (not shown) through the sample injection cup 60, through a valve V1, through the flow cell analyzer 62 and then to a suitable waste disposal site. Sample is pressured into the sample injection cup 60 via a cup analysis probe 138 (described below). In the sample injection cup 60, the sample is mixed with reagent as the reagent is pumped by the reagent pump module 65 through the sample injection cup 60 and is carried therewith through valve V1 and into the flow cell analyzer 62. A $CO_2$ acid reagent pump module 67, capable of pumping $CO_2$ acid reagent directly into the flow cell analyzer 62, is disposed in fluid tight communication with a source of $CO_2$ acid reagent (not shown). Also, a reference solution pump module 69 is disposed in fluid tight communication with a source of reference solution (not shown). The reference solution pump module 69 is capable of pumping reference solution through valve V2 directly into the flow cell analyzer 62.

With this configuration of the ion selective analyzing station 22, reference solution, following each sample analysis, can be delivered from the reference solution pump module 69 into the flow cell analyzer 62 through the valve V2. Measurement of the concentrations of sodium, potassium, calcium, chloride, and carbon dioxide in the reference solution can be performed to check electrode drifts. Since sample pick-up via the probe 138 is operated independently from the reference solution pump module 69, it can be used to deliver sample aliquots to the reaction cup modules 58 while the reference solution pump module 69 is delivering reference solution into the flow cell analyzer 62.

Figure 8:
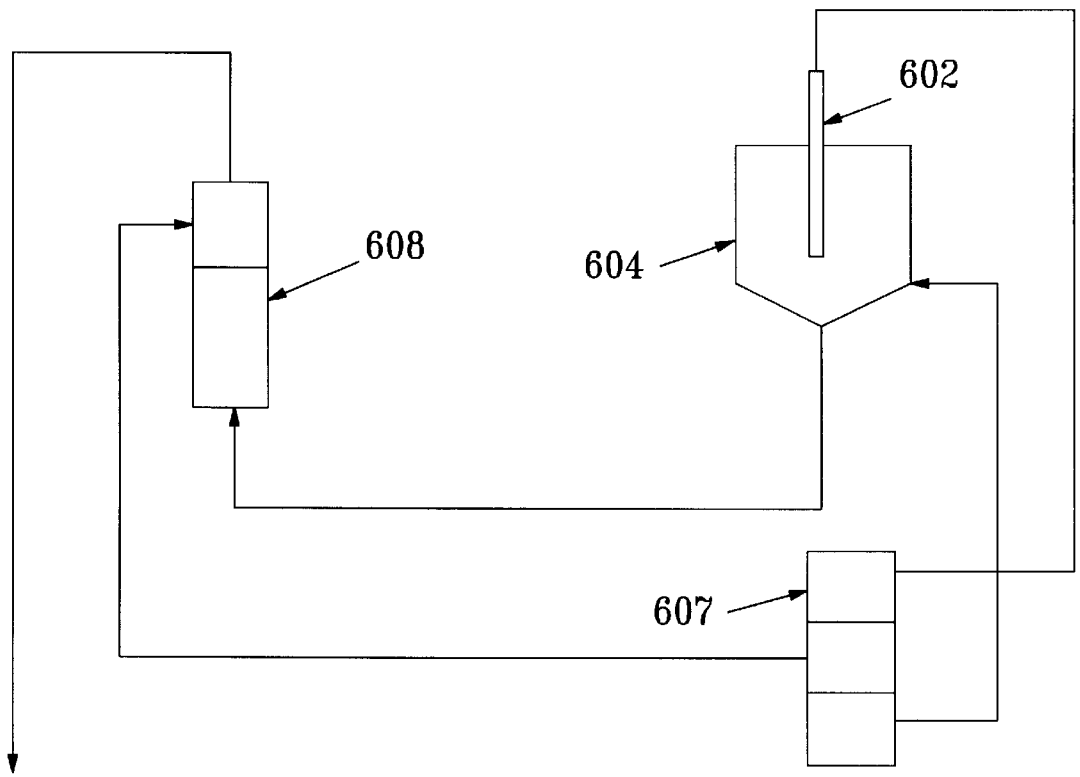
FIG. 8 is a flow diagram illustrating an ion selective reaction cup assembly of the prior art.

The flow scheme of the ion selective analyzing station 22 illustrated in FIG. 7 is contrasted with the flow scheme of a typical ion selective analyzing station of the prior art, as illustrated in FIG. 8. Unlike in the flow scheme of the invention, in the flow scheme of the prior art, sample probe 602 is connected directly to reference pump 607. In a reference measurement cycle, the reference solution delivery to the flow cell 608 is accomplished by using the sample probe 602 via the sample injection cup 604. Because the sample 602 serves as a seal for the sample injection cup 604, the sample probe 602 must stay at the injection cup 604 to complete the reference delivery. Thus, the probe 602 cannot be used to deliver sample aliquots to other cup modules at the same time. As a result, the speed of the overall analysis operation is greatly reduced.

In a preferred embodiment of the ion selective analyzing station 22 of the invention, the sample injection cup 60 is combined in a single unit 702 with the first valve V1 and the second valve V2. FIG. 9 illustrates such a combination 702. The reaction cup 60 constitutes the upper portion of the combination 702. The first valve V1 and the second valve V2 (not shown) are disposed in the lower portion 703 of the combination 702. The sample injection cup 60 has a vertical open bore 704 to provide access to a sample cup mixing chamber 706 by the cup analysis probe 138. The bore 704 has an upper conically-shaped moiety 708 and a lower cylindrically-shaped moiety 710. At the very base of the bore 704, the bore 704 communicates with the sample injection cup mixing chamber 706 through an O-ring 711. The O-ring 711 seals the tip of the cup analysis probe 138 when the probe 138 is inserted through the bore 704 and into the sample injection cup mixing chamber 706.

FIG. 10 illustrates the sample injection cup and valve combination 702 schematically. As illustrated in FIG. 10, the first and second valves V1 and V2 each comprise a valve chamber 712, a flexible membrane 714 and a flexible membrane activator 716. Each valve chamber 712 has a valve inlet opening 718, a valve outlet opening 720 and a valve seat 722. The flexible membrane 714 is disposed within the valve chamber 712 proximate to the valve seat 722. In a typical embodiment, the flexible membrane is made from Mylar® or other similar materials.

The flexible membrane activator 716 is disposed within each valve V1 and V2 such that the activator 716 can alternatively (1) exert pressure on the flexible membrane 714, so as to cause the membrane 714 to flex to a first membrane position wherein the membrane 714 is tightly disposed against the valve seat 722 (whereby, no liquid is allowed to flow through the valve V1 or V2), and (2) withdraw pressure from the flexible membrane 714, so as to cause the membrane 714 to flex to a second membrane position wherein the membrane 714 is not disposed against the valve seat 722 (whereby, liquid is allowed to flow through the valve V1 or V2). The flexible membrane activator 716 is activatable by an energy source which is typically an air/vacuum combination such as in the embodiment illustrated in FIG. 10. In this air/vacuum combination, the combination of pressurized air from an air conduit 724 and vacuum from a vacuum line 726 is alternatively applied to the valves V1 and V2 using air/vacuum switches 728 and 730, respectively. Alternative energy sources, such as electricity, can also be used.

Preferably, the activator 716 is constructed so that, in the event of a failure of the energy source, the activator 716 flexes the membrane 714 to the first membrane position. In the embodiment illustrated in FIG. 10, this is accomplished by a spring 732 which biases the activator 716 to move the flexible membrane 714 to the first membrane position when no energy is provided to the activator 716 by the energy source.

A first conduit 734 connects the sample cup mixing chamber 706 in fluid tight communication with the flow cell 62 and a second conduit 736 connects a source of flushing liquid to the flow cell 62. The first conduit 734 comprises a first moiety 738 which is disposed between a sample cup outlet opening 740 and the first valve V1, an intermediate moiety 742 which is disposed between the first valve V1 and the juncture 744 with the second conduit 736 and a third moiety 746 which is disposed between the juncture 744 and the flow cell 62. The second conduit 736 has a first moiety 748 disposed between the reference solution pump module 69 and the second valve V2 and a second moiety 750 disposed between the second valve V2 and the juncture 744 with the first conduit 734. It is preferable that the combined length of the intermediate moiety 742 of the first conduit 734 and the second moiety 750 of the second conduit 736 be as short as possible. This is because this total length of the conduit is not readily flushed during normal operation. Accordingly, it is preferable in the invention that the juncture 744 of the second conduit 736 with the first conduit 734 be immediately downstream of the first valve V1.

Reagent is pumped into the sample cup 60 from the reagent pump module 65 via reagent conduit 751. Waste is removed from the sample cup mixing chamber 706 via waste removal conduit 753.

A flushing conduit 755 is provided in fluid tight communication with the vertical bore 704. This flushing conduit 755 can be used to provide flushing liquid, such as deionized water, to the vertical bore 704 to allow washing of the tip of the cup analysis probe 138 as the probe 138 is retracted from the vertical bore 704.

The pump 64 has a plurality of discreet pump modules driven by a single pump motor 752. In the embodiment illustrated in FIG. 11, the pump 64 comprises three pump modules 65, 67 and 69. Each of the pump modules 65, 67 and 69 comprises a central bore 754 aligned along a longitudinal axis 756, an inlet/outlet opening 758 and an inlet/outlet conduit 760.

A reciprocatable piston 762 is disposed within the central bore 754 disposed along the longitudinal axis 756. The piston 762 has a first piston moiety 764, a second piston moiety 766 and a third piston moiety 768. The piston 762 is assembled within the piston bore 754 so as to seal the pump modules 65, 67 and 69 from one another.

The pump motor 752 is adapted to reciprocate the piston 762 within all of the central bores 754.

Each pump module 65, 67 and 69 further comprises a 3-way valve 774 for controlling flow in and out of the inlet/outlet conduit 760. Each 3-way valve 774 is connected in fluid tight communication to an inlet conduit 776 and an outlet conduit 778.

The pump 64 further comprises a controller 782 for controlling the pump motor 752 and each of the valves 774 so that, in each of the pump modules 65, 67 and 69, liquid from a source of liquid is drawn into the central bore 754 via the inlet conduit 776 as the piston 762 is retracted, and is then pumped out of the central bore 754 via the outlet conduit 778 as the piston 762 is extended. By adjusting the relative diameters of the central bores and the piston moieties, the flow rates of the several pump modules 65, 67 and 69 can be adjusted to remain in predetermined constant ratios with respect to one another.

Preferably, each of the valves 774 comprises a pair of valve seats 782, a flexible diaphragm 784 and a flexing mechanism 786. The flexible diaphragm 784 is disposed opposite the valve seats 782 and is capable of being flexed between (1) a first diaphragm position, wherein the diaphragm 784 is sealed against the first of the valve seats 782 but not against the second and (2) a second diaphragm position, wherein the diaphragm 784 is not sealed against the first of the valve seats 782 but is sealed against the second. The flexing mechanism is adapted to alternatively flex the diaphragm 784 between the first diaphragm position and the second diaphragm position.

Preferrably the pump module valves 774 are rocker valves such as illustrated in FIGS. 13A and 13B. The flexing mechanism 786 includes a rocker arm 788 activated by a solenoid mechanism 790. The solenoid mechanism 790 includes an electromagnet assembly 791 and a pivoting iron-containing arm 793. A leaf spring 795 biases the arm towards a lowermost position (as illustrated in FIG. 13B). A coil spring 797 biases one end of the rocker arm 788 towards a lowermost position (as illustrated in FIG. 13A).

When the solenoid mechanism 790 is energized, the electromagnet assembly 791 pulls the iron-containing arm 793 towards it (against the biasing pressure of the leaf spring 795). The coil spring 797 pushes the rocker arm 788 so that the rocker arm 788 acts against the flexible diaphragm 784 to push it towards the first diaphragm position (illustrated in FIG. 13A). When the solenoid mechanism 790 is de-engerized, the leaf spring 795 biases the arm 793 against one end of the rocker arm 788 (against the biasing pressure of the coil spring 797) and pushes the rocker arm 788 so the rocker arm 788 acts against the flexible diaphragm 784 to push it towards the second diaphragm position (illustrated in FIG. 13B). A suitable valve 774 used in the pump 64 is a Burkert Type 127 Miniature Solenoid Valve, as sold by Burkert Fluid Control Systems through IMS West Co. of Santa Ana, Calif.

FIG. 14 is a detailed flow diagram of a preferred embodiment of the ion selective analyzing station 22 of the invention. This embodiment includes a sample injection cup 60 such as illustrated in FIGS. 9 and 10. In the sample injection cup 60, a waste valve 792 is provided to control the flushing of waste material from the sample injection cup 60.

The embodiment illustrated in FIG. 14 further includes a flow cell analyzer 62 comprising electrodes capable of measuring the concentration of calcium ions 794, chloride ions 796, sodium ions 798, potassium ions 800 and carbon dioxide 802 in liquid samples, such as blood samples. In this regard, the flow cell analyzer 62 further includes a sodium ion reference cell 804 and a carbon dioxide reference cell 806.

The ion selective analyzing station embodiment illustrated in FIG. 14 further includes a pump 64 such as illustrated in FIGS. 11–13. The pump 64 comprises three pump modules. A buffer reagent pump module 65 pumps buffer reagent from a source of buffer reagent 808 to the sample injection cup 60. A carbon dioxide acid reagent pump module 67 pumps carbon dioxide acid reagent from a source of carbon dioxide acid reagent 810 to the flow cell analyzer 62. A reference reagent pump module 69 pumps internal reference reagent from a source of internal reference reagent 812 directly to the flow cell analyzer 62.

The embodiment illustrated in FIG. 14 further comprises a separate alkaline buffer reagent pump 814 which pumps alkaline buffer reagent from a source of alkaline buffer reagent 816 to the carbon dioxide reference cell 806.

The embodiment illustrated in FIG. 14 further comprises a waste trap mechanism 818 which draws a vacuum on all waste streams in the system, gathers waste from such waste streams and flushes such waste to a suitable waste disposal center 817.

The embodiment of the ion selective analyzing station 22 illustrated in FIG. 14 can be operated as follows. Sample is delivered to the sample injection cup 60 via the cup analysis probe 138. The cup analysis probe 138 is moved down through the vertical bore 704 until the tip of the cup analysis probe 138 protrudes into the sample cup mixing chamber 706. The O-ring 711 seals the tip of the cup analysis probe 138 so that liquids cannot flow from the sample cup mixing chamber 706 upwards into the vertical bore 704.

With the first valve V1 open and second valve V2 closed, a predetermined amount of buffer reagent is pumped by the reagent pump module 55 into the sample injection cup mixing chamber 706 via the reagent conduit 751. As the reagent is pumped into the sample cup mixing chamber 706, sample within the cup analysis probe 138 is ejected into the sample cup mixing chamber 706. Turbulent mixing occurs between the sample and the reagent flowing through the sample cup mixing chamber 706. The combined reagent and sample mixture is then pressured through the first conduit 734 and into the flow cell analyzer 62.

At the same time that reagent is pumped into the sample injection cup 60 by the reagent pump module 55, carbon dioxide acid reagent is pumped by the carbon dioxide acid reagent pump module 57 into the carbon dioxide analysis cell 802 in the flow cell analyzer 62.

Also at the same time that reagent is pumped into the sample injection cup 60, reference solution is pumped by the reference solution pump module 59 to the sodium ion reference cell 804 in the flow cell analyzer 62.

Alkaline buffer reagent is also pumped by the carbon dioxide reference solution pump 814 to the carbon dioxide reference cell 806 in the flow cell analyzer 62.

The flow cell analyzer 62 simultaneously determines the sample concentration of sodium ions, calcium ions, potassium ions, chloride ions and carbon dioxide.

After the analysis of the sample is complete, the first valve V1 is closed and the second valve V2 is opened so as to allow reference solution to flow into the first conduit 734 via the second conduit 736 and thereby flush the system clean with reference solution in preparation for a new analysis cycle.

All of the flushing solutions are drawn out of the system by vacuum applied to the waste trap mechanism 818. From the waste trap mechanism 815, all of the flushing materials are transferred to a suitable waste facility 817.

The cup analysis probe 138 is meanwhile retracted from the sample cup mixing chamber 706 and is prepared to travel to the sample station 14 to retrieve a new sample for analysis. As the cup analysis probe 138 is retracted through the vertical bore 704, a cleaning solution, such as deionized water, is sprayed against the cup analysis probe 138 via the flushing conduit 755, so as to wash any vestiges of sample and reagent from the exterior of the cup analysis probe tip.

Preferably, the ion electrode analyzing station 22 of the invention can determine the concentration of sodium ions, potassium ions, calcium ions, chloride ions and carbon dioxide in a plurality of liquid samples with a turnaround time of less than about 45 seconds per sample, most preferably, less than about 40 seconds per sample.

In the embodiment of the analyzing machine 10 shown in FIGS. 1–6, the analyzing machine 10 further comprises a sample container loading and preparation assembly 68. The loading and preparation assembly 68 comprises a loading mechanism 70 for loading one or more sample containers from a loading area 72 to the sample station 14 along a loading mechanism path 74. The loading mechanism 70 comprises an on-load tray 76 and an off-load tray 78. In the embodiment shown in FIG. 1, the on-load tray 76 and the off-load tray 78 are sized and dimensioned to retain a plurality of sample container racks 34. The on-load tray 76 has a motorized loading arm 80 for pushing a plurality of sample container racks 34 towards the loading mechanism path 74. The off-load tray 78 has a motorized unloading arm (not shown) for pushing the sample container racks 34 away from the loading mechanism path 74.

The loading mechanism path 74 has a motorized loading path arm 82 which moves a single sample container rack 34 along the loading mechanism path 74 on to and off from the sample station 14. A bar code reader 84 is typically disposed along the loading mechanism path 74. The bar code reader 84 is capable of reading bar coded information disposed on each individual sample container 32 as the sample container 32 moves along the loading mechanism path 74.

In the embodiment shown in FIG. 1, the sample container loading and preparation assembly 68 further comprises a sample container cap piercing mechanism 86 capable of piercing the sample container caps 36 so as to leave the caps 36 open for access by the sample extraction cup analysis probes (described below). Such a cap piercing mechanism 86 is disclosed in detail U.S. patent application Ser. No. 08/746,649, entitled AUTOMATIC CHEMISTRY ANALYZER WITH SAMPLE CUP PIERCING ASSEMBLY (presently pending), filed contemporaneously herewith, and which is incorporated herein by reference in its entirety.

As illustrated in FIGS. 2 and 3, the sample container cap piercing mechanism 86 can be disposed under a sample cap piercing mechanism cover 88.

Figures 5A, 5B, 5C:
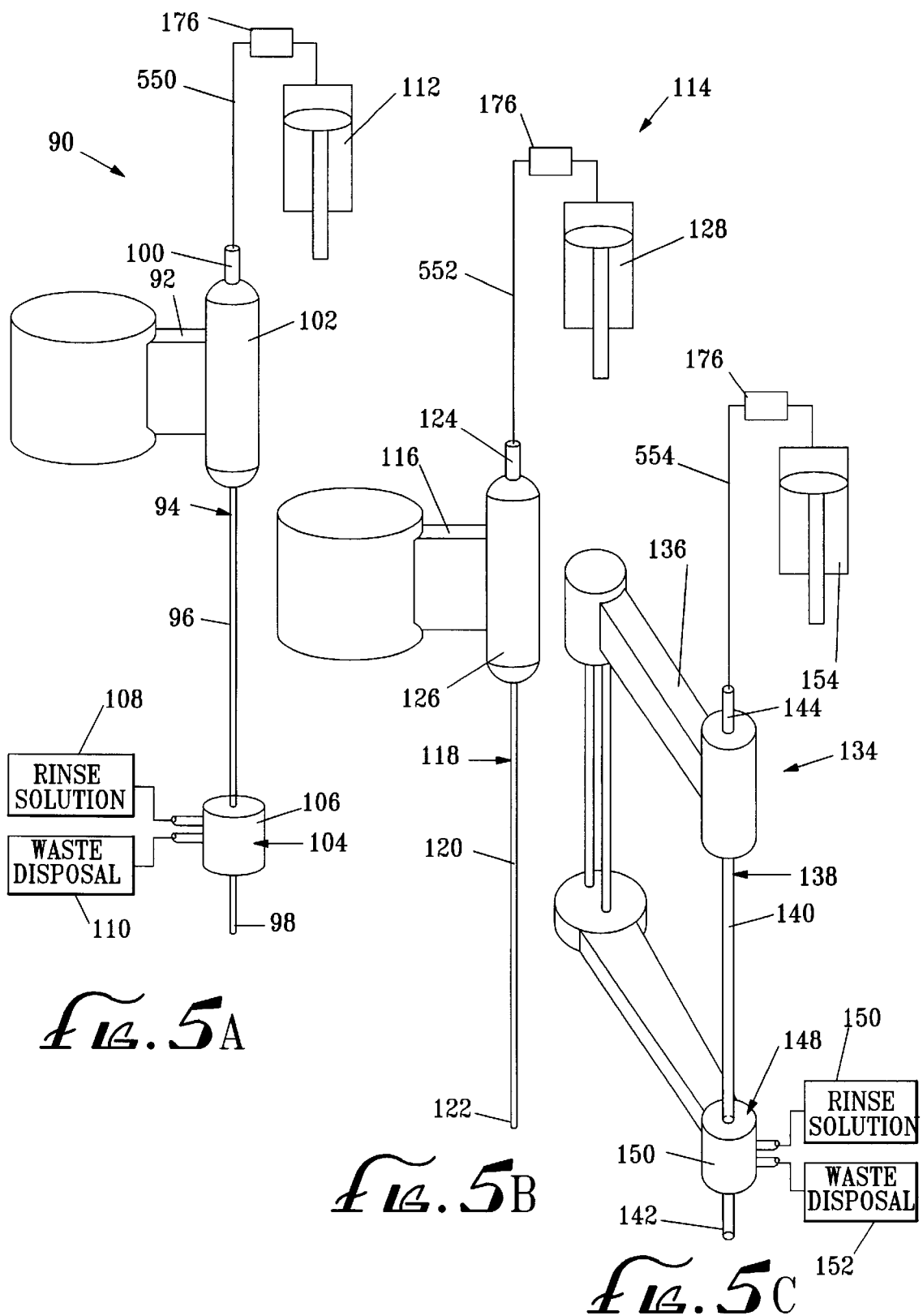
FIG. 5A is a perspective view of a sample probe arm assemble useful in the invention.
FIG. 5B is a perspective view of a reagent probe arm assembly.
FIG. 5C is a perspective view of a cup analyze probe arm assembly.

The analyzing machine 10 further comprises a motorized sample probe arm assembly 90 such as shown in FIG. 5A. The sample probe arm assembly 90 includes a sample probe arm 92 and a hollow sample probe 94. The sample probe 94 has an internal chamber 96, an open lower end 98 and an open upper end 100. The sample probe 94 is disposed generally vertically in the sample probe arm 92 and is movable by a sample probe motor 102 between a lower sample probe position and an upper sample probe position.

The sample probe 94 can be equipped with a sample probe tip cleaning assembly 104 such as is described in U.S. Pat. No. 5,408,891, the entirety of which is incorporated herein by this reference. Such cleaning assembly 104 includes a cleaning assembly chamber 106 connected in fluid tight communication with a source of cleaning liquid 108 and a disposal site 110.

The sample probe arm 92 is movable by a sample probe arm motor (not shown) between a first sample probe arm position wherein the sample probe is immediately above the sample extraction site 38 and a second sample probe arm position wherein the sample probe is immediately above the cuvette sample deposit site 50.

The sample probe 94 is connected to a sample probe pressure altering mechanism capable of alternatively applying a positive pressure and a negative pressure to the internal chamber 96 of the sample probe 94. Such pressure altering mechanism can be any of the various pressure altering mechanisms known in the art. Typically, such pressure altering mechanisms are provided by a syringe pump 112.

The sample probe arm assembly 90 is used to extract a predetermined quantity of sample from sample container 32 disposed within the sample station 14 at the sample extraction site 38 and transport that quantity of sample to a cuvette 44 disposed within the random access analyzing station 18 at the cuvette sample deposit site 50.

The analyzing machine 10 further comprises a motorized reagent probe arm assembly 114 such as shown in FIG. 5B. The reagent probe arm assembly 114 includes a reagent probe arm 116 and a hollow reagent probe 118. The reagent probe 118 has an internal chamber 120, an open lower end 122 and an open upper end 124. The reagent probe 118 is disposed generally vertically in the reagent probe arm 116 and is movable by a reagent probe motor 126 between a lower reagent probe position and an upper reagent probe position.

The reagent probe arm 116 is movable by a reagent probe arm motor (not shown) between a first reagent probe arm position wherein the reagent probe 118 is immediately above the reagent extraction site 42 and a second reagent probe arm position wherein the reagent probe is immediately above the cuvette reagent deposit site 52.

The reagent probe 118 is connected to a reagent probe pressure altering mechanism capable of alternatively applying a positive pressure and a negative pressure to the internal chamber 120 of the reagent probe 118. Such pressure altering mechanism can be any of the various pressure altering mechanisms known in the art. Typically, such pressure altering mechanisms are provided by a syringe pump 128.

The reagent probe arm 116 is used to extract a predetermined quantity of reagent from a reagent container 40 disposed within the reagent station 16 at the reagent extraction site 42 and transport that quantity of reagent to a cuvette 44 disposed within the random access analyzing station 18 at the cuvette reagent deposit site 52.

Both the sample probe arm 92 and the reagent probe arm 116 can include multiple independently movable probes. In the embodiment illustrated in the drawings, both the sample probe arm 92 and the reagent probe arm 116 comprise a pair of probes each independently movable about a primary axis of rotation 130. Both probe arms are also rotatable as a whole about a secondary axis of rotation 132.

The analyzing machine 10 further comprises a cup analysis probe arm assembly 134 such as shown in FIG. 5C. The cup analysis probe arm assembly 134 includes a cup analysis probe arm 136 and a hollow cup analysis probe 138. The cup analysis probe 138 has an internal chamber 140, a lower end 142 and an open upper end 144. The cup analysis probe 138 is disposed generally vertically in the cup analysis probe arm 136 and is movable by a cup analysis probe motor (not shown) between a lower cup analysis probe position and an upper analysis probe position.

The cup analysis probe 138 can be equipped with a cup analysis probe tip cleaning assembly 146 such as is known in the prior art. Such cleaning assembly includes a cleaning assembly chamber 148 connected in fluid tight communication with a source of cleaning liquid 150 and a disposal site 152.

The cup analysis probe arm 136 is movable by a cup analysis probe arm motor (not shown) between a first cup analysis probe arm position wherein the cup analysis probe is immediately above a sample container 32 in the sample station 14, a second cup analysis probe arm position wherein the cup analysis probe 136 is immediately above one of the reaction cup modules 58 and a third cup analysis probe arm position wherein the cup analysis probe 136 is immediately above the sample injection cup 60.

The cup analysis probe 136 is connected to a cup analysis probe pressure altering mechanism capable of alternatively applying a positive pressure and a negative pressure to the internal chamber 140 of the cup analysis probe 136. Such pressure altering mechanism can be any of the various pressure altering mechanisms known in the art. Typically, such pressure altering mechanisms are provided by a syringe pump 154.

The cup analysis probe arm assembly 134 is used to extract a predetermined quantity of sample from a sample container 32 disposed within the sample station 14 and transport that quantity to each of the reaction cup modules 58 and to the sample injection cup 60.

The analyzing machine 10 further comprises a cuvette stirring rod assembly 156 such as shown in FIG. 5D. The cuvette stirring rod arm assembly 156 includes an elongate rotatable cuvette stirring rod 158 having a lower end 160 and an upper end 162. The lower end 160 of the cuvette stirring rod includes a cuvette stirring rod paddle 164 attached thereto. The cuvette stirring rod is generally disposed vertically and is movable between a lower cuvette stirring rod position and an upper stirring rod position. The cuvette stirring rod arm assembly 156 is positionable above the cuvette mixing site 54. As illustrated by the embodiments shown in the drawings, the motorized cuvette stirring rod assembly 156 can be an independent and separate assembly or it can be integrated with the sample probe arm 92 and/or the reagent probe arm 116.

The analyzing machine 10 further comprises a cuvette wash station 166 as shown in FIG. 5E. The cuvette wash station probe 168 is used to extract liquid reaction mixtures from the cuvettes 44, dispose such mixtures to a suitable disposal site and then rinse and clean the cuvette 44 so that it can be used to analyze another quantity of sample.

The wash station 166 comprises one or more motorized cuvette wash station probes 168. Each wash station probe 168 has an internal chamber 170, an open lower end 172 and an open upper end 174. The wash station probe 168 is disposed generally vertically above the cuvette washing site 56 in the random access analyzing station 18 and is movable by a wash station probe motor (not shown) between a lower wash station probe position and an upper wash station probe position.

In the embodiment shown in the drawings, the wash station probes 168 operated in pairs, one of each pair of wash station probes 168 being connected to a source of pressurized rinse solution and the other wash station probe 168 of each pair being connected to a disposal system adapted to vacuum out the contents of a cuvette and transfer such contents to a suitable disposal site.

Alternatively, each individual wash station probe 168 can be connected to a wash station probe pressure altering mechanism capable of alternatively applying a positive pressure and a negative pressure to the internal chamber 170 of the wash station probe 168. The wash station probe pressure altering mechanism includes a mechanism for providing pressurized washing liquid from a source of washing liquid to the wash station probe 168 for washing a cuvette disposed at the cuvette washing site 56 and a mechanism for providing a negative pressure to the interior chamber 170 of the wash station probe 168 for removing waste liquids from a cuvette disposed at the cuvette washing site 56 and for transferring such waste liquids to a disposal site. Such a mechanism for providing negative pressure to the interior chamber 170 typically comprises a source of vacuum.

Each of the pressure altering mechanisms usable in the analyzing machine can further comprise an obstruction detector 176 comprising a pressure detector 502 operatively installed within the operative pressure transmitting conduits to alert the operator and/or shut down the machine should an obstructive pressure drop be detected within the pressure altering mechanism. Such an obstruction detector 176 is described in detail in U.S. patent application Ser. No. 08/748,135, entitled AUTOMATIC CHEMISTRY ANALYZER WITH OBSTRUCTION DETECTION SYSTEM (presently pending), filed contemporaneously herewith, and which is incorporated herein in its entirety.

Typically, the automated analyzing machine 10 further comprises a controller 178 for controlling each of the various motors in a way which provides for the smooth, efficient and rapid operation of the machine 10. The control is typically also used to retain and report analysis data. Preferably, the controller 178 comprises a digital computer which can be preprogrammed with a large variety of operating instructions depending upon the samples being analyzed, the analyses to be run and the reagents at hand. Most preferably, the digital computer receives bar coded information regarding each of the samples to be analyzed, and the reagents in the reagent station 16 and uses that information to most efficiently conduct the analyses. Also, it is preferable that the controller 178 keep track of the amounts of reagents used so as to alert the operator whenever reagent in any particular reagent container 40 begins to run low.

Also, it is preferable that the controller 178 include a "stat" mode, which gives the operator the ability to require the machine 10 to analyze particularly important samples in the reaction cup and ion selective electrode analyzing stations ahead of all other samples.

In operation, the operator of the automated analyzing machine of the invention 10 places samples to be analyzed in individual sample containers 32 and places each sample container 32 in one or more sample container racks 34. The sample container racks 34 are placed in the on-load tray 76.

The motorized loading arm 80 pushes sample container racks 34 in the on-load tray 76 towards the loading mechanism path 74. As each sample container rack 34 enters the loading mechanism path 74, the motorized loading path arm 82 pushes the sample container rack 34 along the loading mechanism path 74 towards the sample station 14.

As the sample containers 32 pass by the bar code reader 84, bar-coded information appended to each sample container 32 is read by the bar code reader 84 and is transmitted to the controller 178. Such bar code coded information typically includes the identity of the sample and the analyses which are to be run using individual portions of the sample.

As the sample container rack 34 is pushed further along the loading mechanism path 74, it passes under the cap piercing mechanism 86. The cap piercing mechanism 86 pierces the caps 36 on each of the sample containers 32.

The sample container rack 34 then is loaded into the sample station 14 wherein a clamping mechanism within the sample station 14 holds the sample container rack 34 firmly upright.

The sample station 14 is rotated under the control of the controller 178. When an individual sample container 32 is placed at a sample extraction site 38, a small quantity of the sample is extracted from the sample container 32 by the sample probe 94. This is accomplished by positioning the sample probe 94 above the sample extraction site 38, lowering the sample probe 94 to the lower sample probe position wherein the open-ended lower end 98 of the sample probe 94 is placed below the surface of the sample within the sample container 32. A small quantity of the sample is then extracted into the sample probe internal chamber 96 by drawing a vacuum on the sample probe internal chamber 96 using the sample probe pressure altering mechanism. The sample probe 94 is then raised to the upper sample probe position and the sample probe arm 92 moves the sample probe 94 to a position where it is directly above the cuvette sample deposit site 50.

At the cuvette sample deposit site 50, the sample probe 94 is again lowered to the lower sample probe position and the quantity of sample within the sample probe 94 is deposited into a cuvette 44 positioned at the cuvette sample deposit site 50. This is done by creating a slight elevated pressure within the sample probe internal chamber 96 using the sample probe pressure altering mechanism. The lower end of the sample probe 94 is then retracted into the sample probe tip cleaning assembly 104 where it is rinsed using cleaning liquid from the source of cleaning liquid 108. After cleaning, the cleaning liquid is flushed to a suitable disposal site 110. The sample probe 94 is then ready to extract another quantity of sample from another sample container 32.

Contemporaneously with the above-described action of the sample probe 94, the reagent probe 118 is used in similar fashion to extract a quantity of an appropriate pre-mixed reagent from the reagent station 16 and depositing that quantity of reagent into the cuvette 44. Usually the reagent is added to the cuvette immediately prior to the deposit of the sample within the cuvette 44.

After sample and reagent are both added to the cuvette 44, the cuvette 44 is rotated to the cuvette mixing site 54. At the cuvette mixing site 54, the cuvette stirring rod 158 is lowered to the lower cuvette stirring rod position and the stirring rod paddle 164 is rotated so as to agitate and thoroughly mix the sample and reagent within the cuvette 44.

In typical random access analyzing operations wherein analyses are carried out at an elevated temperature, the mixture of sample and reagent within the cuvette 44 is then allowed to stand within the random access analyzing station 18 while the mixture is brought up to temperature, such as by blowing heated air through the random access analyzing station 18. When the mixture within the cuvette 44 has reached proper temperature, the contents of the cuvette 44 are analyzed using the random access analyzing station analyzer 46. In a preferred operation, the cuvette 44 is placed at the random access analyzing station analyzing site 46 a plurality of times and is thereby analyzed a plurality of times so that the reportable results are derived from an average of the plurality of analyses. The reportable results are thereby extremely reliable.

After analyses are completed regarding the mixture within the cuvette 44, the cuvette 44 is moved to the cuvette washing site 56 at the cuvette wash station 166. At the cuvette wash station 166, a wash station probe 168 is moved from its upper probe position to the lower probe position and the reaction mixture is extracted using the wash station pressure altering mechanism. Depending upon the kind of mixture which had been analyzed within the cuvette 44, the cuvette 44 is then rinsed once or several times using pressurized washing liquid. After the rinse liquid is removed from the cuvette 44 and sent to suitable disposal, the cuvette 44 is ready to accept another sample for analysis.

Contemporaneously with the operation of the random access analyzing station 18, high volume analyses are performed in the reaction cup analyzing station 20 and in the ion selective electrode analyzing station 22. First, a predetermined quantity of an appropriate reagent is pumped into each reaction cup 332 and into the injection sample cup 60 using the reagent pump 59. The magnetic stirrer is engaged. Then, the cup analysis probe arm assembly 134 positions the cup analysis probe 136 above a sample container 32 within the sample station 14, the cup analysis probe 136 is lowered to the lower probe position and a relatively large quantity of sample is extracted into the internal chamber 140 within the cup analysis probe 138 using the cup analysis probe pressure altering mechanism. The cup analysis probe 138 is then raised to the upper probe position and the cup analysis probe arm 136 moves the cup analysis probe 138 to a position directly above one of the reaction cup modules 58. The cup analysis probe 138 is lowered to the lower cup position and a portion of the sample within the cup analysis probe 138 is deposited within the reaction cup 332. The cup analysis probe 138 is then again raised to the upper probe position and the cup analysis probe arm 136 moves the cup analysis probe 138 to immediately above each of the other reaction cup modules 58 and deposits a portion of the sample within each such reaction cups 332.

When all of the reaction cups 332 are filled, the cup analysis probe arm 136 moves the cup analysis probe 138 to directly above the sample injection cup 60. The cup analysis probe 138 is again lowered to the lower probe position and the remainder of the sample is deposited within the injection sample cup 60.

After the mixture of reagent and sample is thoroughly mixed by the magnetic stirrer, the mixture is analyzed using the reaction cup analyzing station analyzer 334 in each cup module, and the results of the analyses are reported to the controller 178. The reaction cups 332 are then rinsed and ready for another sample.

Contemporaneously, in the ion specific electrode analysis station, the quantity of sample within the injection sample cup 60 is thoroughly flow mixed with the reagent. After the sample and reagent are properly mixed, the mixture is passed through the flow cell 62 where individual electrodes within the flow cell 62 each perform a single analysis on the mixture. The results of the analysis are reported to the controller 178. The mixture is then drained to a suitable disposal site 66 and the system is rinsed in preparation for the analysis of another sample.

After the sample within each of the sample containers 32 in a sample container rack 34 are analyzed, the sample container rack 34 is removed from the sample station 14 using the motorized loading path arm 82. The sample container rack 34 is retracted along the loading mechanism path 74 to the off-load tray 78. Once in the off-load tray 78, the motorized unloading arm pushes the sample container rack 34 towards the end of the off-load tray 78 where it is removed by the operator.

The invention provides significant improvements over the prior art by reducing throughput times, maintenance costs and operating expense, while increasing accuracy and reliability.

Although the present invention has been described in considerable detail with reference to certain preferred versions thereof, other versions are possible. Therefore, the spirit and scope of the appended claims should not be limited to the description of the preferred versions contained herein.

What is claimed is:

1. An ion selective electrode analyzing combination comprising:
   (a) a sample injection cup having a sample cup mixing chamber and a sample cup outlet opening;
   (b) a flow cell for measurement of different electrolytes in a liquid sample, the flow cell having a flow cell inlet opening and a flow cell outlet opening;
   (c) a pump having a plurality of discrete pump modules and a first pump motor for driving all of the pump modules, each pump module having a pumping module inlet opening and a pump module outlet opening;
   (d) a first conduit for connecting the sample injection cup outlet opening in fluid tight communication to the flow cell inlet opening, the first conduit having therein a first valve disposed proximate to the sample cup outlet opening; and
   (e) a second conduit for connecting the outlet opening of one of the pumping modules to the first conduit at a location immediately downstream of the first valve, the second conduit having therein a second valve.

2. The ion selective electrode analyzing combination of claim 1 wherein the combination is capable of determining the concentration of sodium, potassium, calcium, chloride and carbon dioxide in a liquid sample.

3. The ion selective electrode analyzing combination of claim 1 wherein the combination is capable of determining the concentration of sodium, potassium, calcium, chloride and carbon dioxide in a plurality of liquid samples with a turnaround time of less than about 45 seconds per sample.

4. The ion selective electrode analyzing combination of claim 1 wherein the combination is capable of determining the concentration of sodium, potassium, calcium, chloride and carbon dioxide in a plurality of liquid samples with a turnaround time of about 40 seconds per sample.

5. The ion selective electrode analyzing combination of claim 1 wherein the first and second valves each comprise:
   (a) a valve chamber having a valve inlet opening, a valve outlet opening and a valve seat;
   (b) a flexible membrane disposed within the valve chamber proximate to the valve seat; and
   (c) an activator for alternatively (1) exerting pressure on the membrane so as to cause the membrane to flex to a first membrane position wherein the membrane is tightly disposed against the valve seat and no liquid is allowed to flow through the valve and (2) withdrawing pressure from the membrane so as to cause the membrane to flex to a second membrane position wherein the membrane is not disposed against the valve seat and liquid is allowed to flow through the first valve, the activator being activatable by an energy source and the activator being constructed such that, in the event of a failure of the energy source, the activator flexes the membrane to the first membrane position.

6. The ion selective electrode analyzing combination of claim 1 wherein the reagent pump is a pump comprising:
   (a) a first pump module having a first inlet/outlet opening and a first central bore, the first central bore being aligned along a longitudinal axis;
   (b) a second pump module having a second inlet/outlet opening and a second central bore, the second central bore being aligned along the longitudinal axis;
   (c) a reciprocatable piston disposed along the longitudinal axis, the piston having a first piston moiety disposed within the first bore and a second piston moiety disposed within the second bore, both first and second piston moieties being shaped with a large diameter section and a small diameter section, the piston being constructed to seal the first pump module from the second pump module;
   (d) a pump motor for reciprocating the piston within the first central bore and the second central bore;
   (e) a first inlet/outlet conduit attached in fluid tight communication with the first inlet/outlet opening and a second inlet/outlet conduit attached in fluid tight communication with the second inlet/outlet opening;
   (f) a first 3-way valve disposed within the first inlet/outlet conduit, and a second inlet/outlet valve disposed within the second inlet/outlet conduit, each of the 3-way valves comprising:
   i) a first valve seat and a second valve seat;
   ii) a flexible diaphragm disposed opposite the valve seats, the diaphragm being capable of flexing between (1) a first diaphragm position wherein the diaphragm is sealed against the first of the valve seats but not against the second and (2) a second diaphragm position wherein the diaphragm is not sealed against the first of the valve seats by is sealed against the second; and
   iii) a flexing mechanism for alternatively flexing the diaphragm between the first diaphragm position and the second diaphragm position; and
   (g) a controller for controlling the pump motor and the flexing mechanism in each of the valves so that liquid from a first source of liquid is pumped at a first flow rate via the first pump module while liquid from a second source of liquid is simultaneously pumped at a second flow rate via the second pump module, the ratio of the second flow rate to the first flow rate being constant.

7. An ion selective electrode analyzing combination comprising:
   (a) a sample injection cup having a sample cup mixing chamber and a sample cup outlet opening;
   (b) a flow cell for measurement of different electrolytes in a liquid sample, the flow cell having a flow cell inlet opening and a flow cell outlet opening;
   (c) a pump comprising:
   i) a first pump module having a first inlet/outlet opening and a first central bore, the first central bore being aligned along a longitudinal axis;
   ii) a second pump module having a second inlet/outlet opening and a second central bore, the second central bore being aligned along the longitudinal axis;
   iii) a reciprocatable piston disposed along the longitudinal axis, the piston having a first piston moiety disposed within the first central bore and a second piston moiety disposed within the second central bore, both first and second piston moieties being shaped with a large diameter section and a small diameter section, the piston being constructed to seal the first pump module from the second pump module;
   iv) a pump motor for reciprocating the first piston within the first central bore and the second central bore;

v) a first inlet/outlet conduit attached in fluid tight communication with the first inlet/outlet opening and a second inlet/outlet conduit attached in fluid tight communication with the second inlet/outlet opening;

vi) a first 3-way valve disposed within the first inlet/outlet conduit, and a second inlet/outlet valve disposed within the second inlet/outlet conduit, each of the 3-way valves comprising:

I) a first valve seat and a second valve seat;

II) a flexible diaphragm disposed opposite the valve seats, the diaphragm being capable of flexing between (1) a first diaphragm position wherein the diaphragm is sealed against the first of the valve seats but not against the second and (2) a second diaphragm position wherein the diaphragm is not sealed against the first of the valve seats by is sealed against the second; and III) a flexing mechanism for alternatively flexing the diaphragm between the first diaphragm position and the second diaphragm position; and vii) a controller for controlling the pump motor and the flexing mechanism in each of the valves so that liquid from a first source of liquid is pumped at a first flow rate via the first pump module while liquid from a second source of liquid is simultaneously pumped at a second flow rate via the second pump module, the ratio of the second flow rate to the first flow rate being a constant;

(d) a first conduit for connecting the sample injection cup outlet opening in fluid tight communication to the flow cell inlet opening, the first conduit having therein a first valve disposed proximate to the sample cup outlet opening; and (e) a second conduit for connecting the outlet opening of one of the pump modules to the first conduit at a location immediately downstream of the first valve, the second conduit having therein a second valve;

wherein the first and second valves each comprise:

i) a valve chamber having a valve inlet opening, a valve outlet opening and a valve seat;

ii) a flexible membrane disposed within the valve chamber proximate to the valve seat; and iii) an activator for alternatively (1) exerting pressure on the membrane so as to cause the membrane to flex to a first membrane position wherein the membrane is tightly disposed against the valve seat and no liquid is allowed to flow through the first valve and (2) withdrawing pressure from the membrane so as to cause the membrane to flex to a second membrane position wherein the membrane is not disposed against the valve seat and liquid is allowed to flow through the first valve, the activator being activatable by an energy source and the activator being constructed such that, in the event of a failure of the energy source, the activator flexes the membrane to the first membrane position.

\* \* \* \* \*